Figure 1:
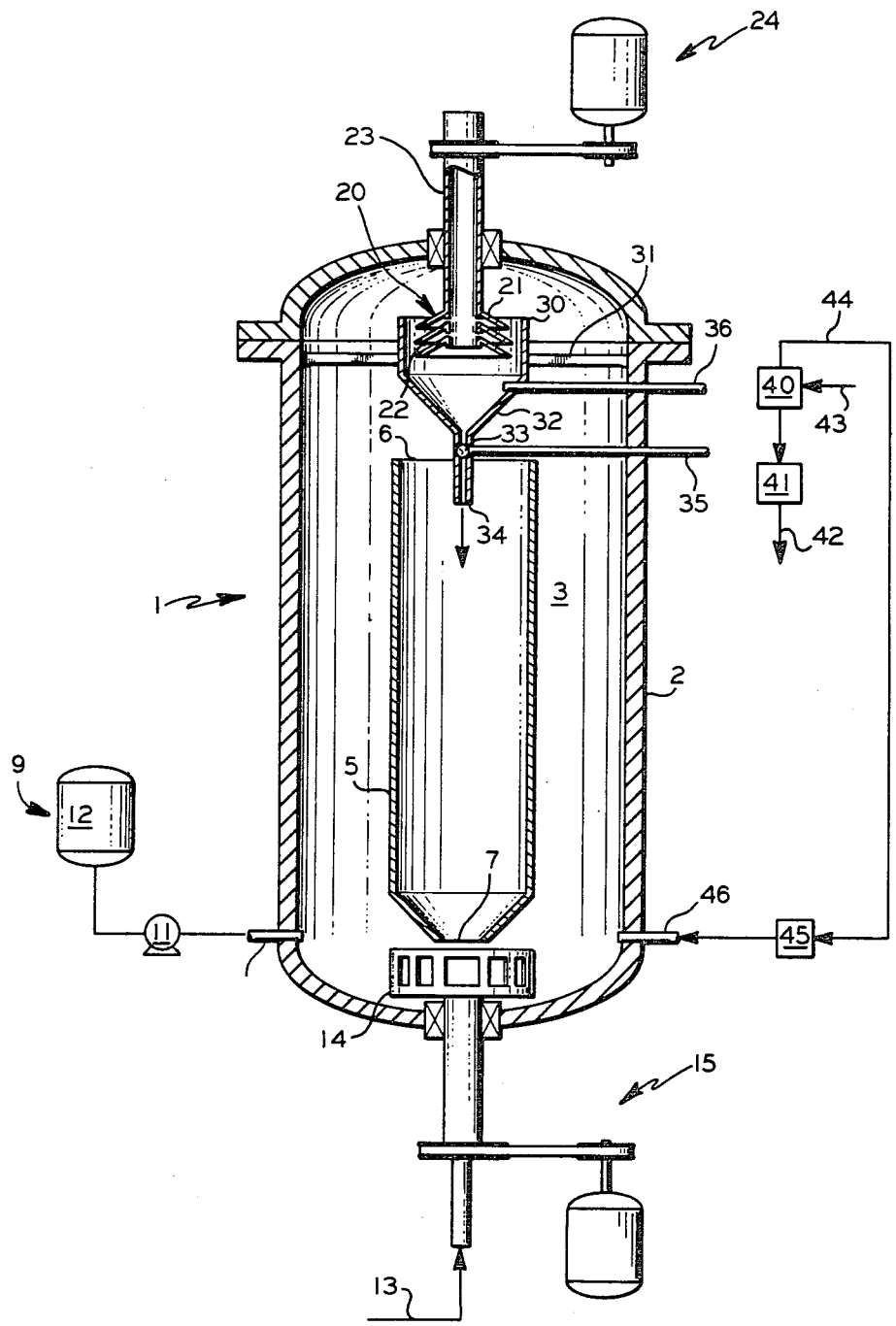

United States Patent [19]

Hitzman

[11] 4,380,584

[45] Apr. 19, 1983

[54] FERMENTATION APPARATUS

[75] Inventor: Donald O. Hitzman, Bartlesville, Okla.

[73] Assignee: Phillips Petroleum Company, Bartlesville, Okla.

[21] Appl. No.: 373,774

[22] Filed: Apr. 30, 1982

Related U.S. Application Data

[62] Division of Ser. No. 139,371, Apr. 11, 1980, Pat. No. 4,340,677.

[51] Int. Cl.³ .................. C12M 1/08; C12M 1/06; C12M 1/04; C12M 1/02
[52] U.S. Cl. .................................. 435/313; 435/314; 435/315; 435/316
[58] Field of Search ............... 435/243, 68, 246, 804, 435/261, 287, 312, 314, 315, 800, 812, 313, 316; 233/13, 17, 18

[56] References Cited

U.S. PATENT DOCUMENTS

| | | | |
|---|---|---|---|
| 2,542,031 | 9/1982 | Humfeld et al. | 435/812 |
| 3,982,998 | 6/1980 | Hitzman et al. | 435/246 |
| 4,342,835 | 8/1982 | Hitzman et al. | 435/243 |

*Primary Examiner*—Raymond N. Jones
*Assistant Examiner*—Elizabeth J. Curtin

[57] ABSTRACT

An organism rich fluid is withdrawn from a foam fermenting apparatus by collecting and withdrawing the fluid from the foam breaker. In another embodiment the fluid from the foam breaker inside of the fermenter is subjected to a liquid/solid centrifugal action and an organism rich fluid stream as well as an organism depleted fluid stream is recovered.

11 Claims, 2 Drawing Figures

FERMENTATION APPARATUS

This application is a division of application Ser. No. 139,371, filed Apr. 11, 1980, now U.S. Pat. No. 4,340,677.

This invention relates to phase separation of sterile mixtures. More specifically, the invention relates to a process and apparatus for separating a mixture containing a gaseous, a liquid and a solid component, particularly foams, in a system involving biological conversion of substances.

BACKGROUND OF THE INVENTION

Biological processes have been used for centuries, for instance, in the production of beer and wine. Recently, single cell protein processes have become a field of significant research among the biological processes. Whereas broadly speaking biological processes include all operations involving reactions between living materials and non-living materials, in the present specification and claims a more limited definition of a biological process is used. Here a biological process is intended to refer to processes involving microorganism fermentation in a fluid environment. Such microorganisms may be, e.g. bacteria or yeasts, and such fluid environments include foam environments.

One well known biological process to which this invention is applicable is a fermentation process for the production of single cell protein. A presently preferred example for such a process is described in U.S. Pat. Nos. 3,642,578 and 3,982,998. Generally, in a single cell protein fermentation process an aerobic fermentation involving a microorganism and a nutrient fluid is carried out in the presence of free oxygen supplied for instance by the injection of air. In a fermenter generally the nutrient fluid together with the microorganism are subjected to gas injection. A foam is formed in the upper portion of the fermenter whereas the lower portion of the fermenter generally contains a liquid. The foam formed is broken in a foam breaker and from this foam breaker gas is removed whereas the fluid remains in the fermenter.

From the bottom of the fermenter a microorganism containing fluid is usually withdrawn, subjected to a solid/liquid separation step, e.g. in a wash centrifuge and the recovered washed microorganism mass is thereafter dried to obtain the final product. The fluid removed during such a solid/liquid separation step contains still valuable ingredients and is therefore generally sterilized and thereafter returned to the fermenter. In the prior art procedures the sterilization of this recycle liquid is necessary to avoid any contamination of the recycled stream. The fluid introduced into the fermenter has to be absolutely sterile in most biological processes, since the smallest contamination with living organisms in the fermenter can destroy the entire reaction and result in undesired products, and a plant shut down and thus increased costs. Therefore, it has been proposed in the art to sterilize all recycled streams. This practice is today followed throughout the industry.

THE INVENTION

It is one object of this invention to provide a new biological process and apparatus for carrying out this process.

A further object of this invention is to improve the biological process involving sterile recycle streams.

Yet another object of this invention is a simplified process for recovery of organisms from a fermenter.

A still further object of this invention is to increase the efficiency of a biological process using basically commercially available equipment.

Another object of this invention is to allow a higher steady state concentration of microorganisms in a fermentation process.

Figure 2:
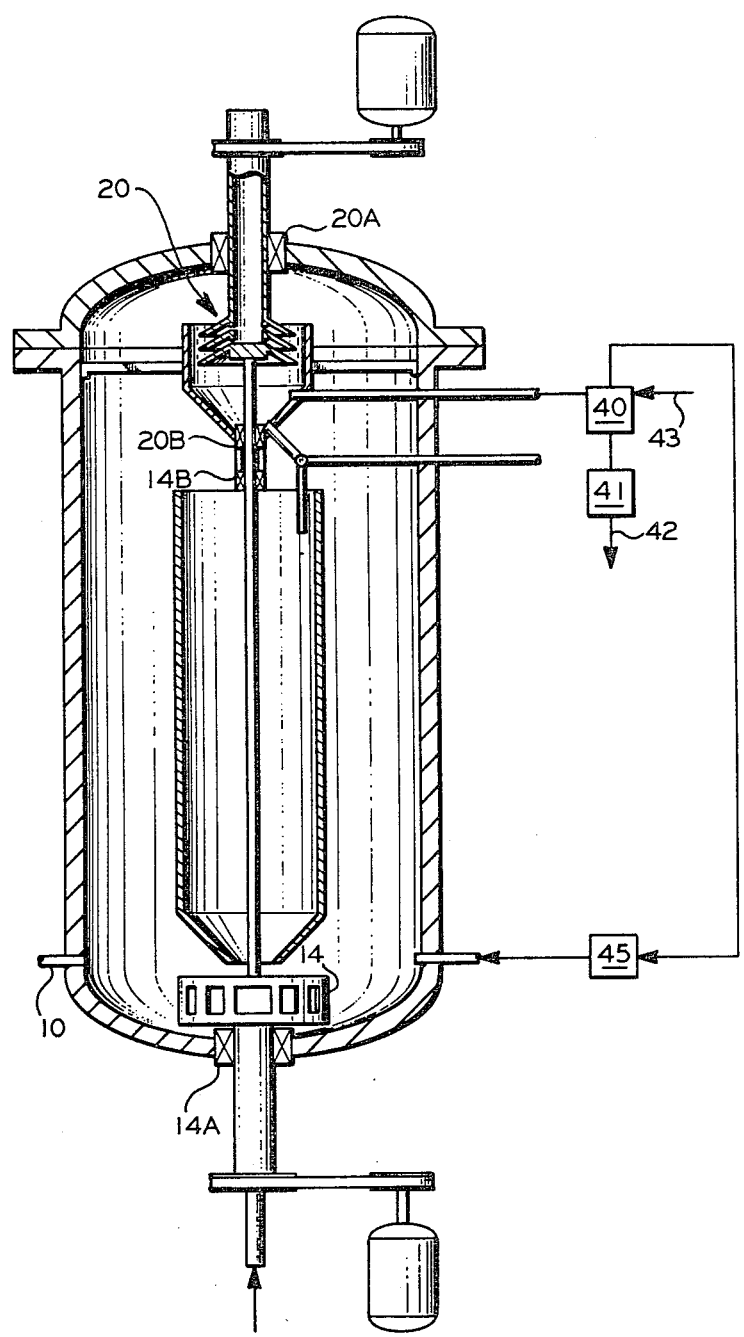

These and other objects, advantages, details, features, and embodiments of this invention will become apparent to those skilled in the art from the following description, the appended claims and the drawing in which FIG. 1 is a schematic cross sectional representation of an apparatus in accordance with this invention, and FIG. 2 is a schematic cross sectional view of another embodiment of the apparatus of the present invention.

In accordance with this invention a fermentation process is provided which distinguishes over the known processes in subjecting the fluid being essentially free of gas coming from the foam breaker to a centrifugal solid/liquid separation action within the fermenter and obtaining a first stream which is depleted of microorganism solids and a second stream which is enriched in microorganism solids.

More specifically, the present invention provides in a first embodiment an improved biological process. The biological process involves the fermentation of a multiphase mass comprising a fluid nutrient phase, a solid organism phase and a gaseous phase. The fermentation is carried out in a fermenter where this mass is subjected to fermentation conditions thereby consuming nutrient and multiplying the organisms. The multiphase mass is present as a foam in said fermenter at least in its upper portion. The foam is subjected to a foam breaking step whereby a gas stream which is essentially free of the fluid nutrient phase and of the solid organism phase as well as a fluid stream is obtained. The fluid stream contains both the fluid nutrient phase and the solid organism phase. Frequently, the organisms concentrate in the foam and therefore the fluid stream from the foam breaking step can be slightly richer in the solid organism phase than the fluid closer to the bottom area of the fermenter.

In accordance with this invention the fluid stream from the foam breaking step is then subjected to a centrifugal action inside of said fermenter. This centrifugal action is basically a solid/liquid centrifugal action and generates a first fluid stream which is rich in the fluid nutrient phase but depleted of said solid organism phase as well as a second fluid stream which in turn is rich in said solid organism phase but depleted of said fluid nutrient phase. These two separated fluid streams in accordance with this invention can be used in a variety of recycle and control embodiments of this invention.

It is particularly preferred to pass said first fluid stream—the stream that is depleted of solids and contains the major portion of the fluid or liquid nutrient phase—directly from said centrifugal operation back into contact with microorganisms in the fermenter. It is also within the scope of this invention to pass this first fluid stream into a second fermenter. The important advantage of this invention in this embodiment resides in the fact that the reinjected fluid never leaves the fermenter or respectively never reaches any environment wherein this first fluid stream can be contaminated. The first fluid stream therefore remains entirely free of contaminating organisms and need not be sterilized again before it can be used in a fermenter again.

The organism enriched fluid stream or the second fluid stream is also biologically noncontaminated and a portion of this stream may be, if desired, introduced into a fermenter.

The process of this invention is applicable in a variety of environments. The preferred embodiment resides in an aerobic fermentation process in which the fermentation is carried out with free oxygen containing gas, such as air, being added to the mixture; other applications include nitrogen addition to the fermentation mixture as well as fermentations with no external gas addition at all wherein the culture itself forms a certain amount of gas, such as $CO_2$.

This invention can be used in biological processes for the production of ethanol, for the production of SCP or any other desired product or byproduct, such as gums. The main product stream may therefore be the solid rich or the solid depleted stream leaving the fermenter-internal centrifuge action. Water-soluble products that may thus be recovered are ethanol and gums. Ethanol withdrawal with all or at least a portion of the organisms from the internal centrifuge action remaining in the fermenter prevents the buildup of a zero-growth ethanol concentration and is therefore desirable in ethanol fermentation.

Presently, the preferred application of this invention lies in the use thereof in a SCP fermentation involving thus withdrawal of at least a portion of the solid rich material leaving the centrifuge action. Thus, the second fluid stream or the microorganism rich stream constitutes at least a portion and in some instances the entire product stream recovered from the fermenter. This stream is subjected to further recovery steps such as a washing and centrifuging step and a drying step to recover dried product.

The nutrient portion of the second solid organism phase rich stream which is separated during this final workup procedure may also be reused but is preferably sterilized before any reintroduction thereof into a fermenter. Further preferred variations of this process will become apparent in connection with the description of the second embodiment of this invention, the fermentation apparatus.

In accordance with this second embodiment of the invention a fermentation apparatus is provided. This fermentation apparatus comprises a housing and at least one feed inlet into said housing and at least one product outlet from said housing. Inside of said housing a foam breaker is arranged in the upper portion thereof. A gas outlet operatively connected to this foam breaker for allowing the removal of the gas is provided for. In accordance with this invention the fermentation apparatus comprises a solid/liquid centrifuge arranged within said housing. This solid/liquid centrifuge is operatively connected to the foam breaker for receiving fluid from this foam breaker. The solid/liquid centrifuge within the housing allows to separate a solids enriched fluid stream and a solid depleted stream from the centrifuge. These streams or portions thereof can directly be introduced into fermenters or reintroduced into the same fermenter without having to sterilize or purify these streams.

In a preferred variation of this embodiment of the invention the foam breaker is a mechanical foam breaker which comprises one or more solid rotatably arranged surfaces. These rotatably arranged surfaces are mechanically connectable to drive means which allow these solid surfaces to be put into rapid rotation. Foam contacting the rapidly rotating surfaces is broken and a fluid stream is spun off from the rapidly rotating surfaces. Also a gas stream is withdrawn from these surfaces. In accordance with the preferred variation of this invention here described the solid/liquid centrifuge comprises a second centrifuge surface arranged within the housing and surrounding the first solid surface. The arrangement of the second centrifuge surface around the foam breaking solid surfaces is such that the fluid spun off from these first solid surfaces of the foam breaker contacts the second centrifuge surface essentially tangentially and thus subjects this fluid which comprises solids and liquid material to a solid/liquid separation whereby the heavier solids are distributed at a higher concentration closer to the centrifuge surface. First receiving conduit means are operatively connected with the second centrifuge surface for receiving therefrom a first fluid stream rich in liquid but depleted in solids and second receiving conduit means are also operatively connected with this second centrifuge surface for receiving therefrom a second fluid stream rich in solids, but depleted in liquid.

Typically, the foam breaker comprises a plurality of axially spaced apart parallel conical surfaces connected to an axial tube with fluid connection being provided between the spaces between these conical surfaces and the interior of the axial tube. The second centrifuge surface is usually an essentially circular cylindrical surface coaxially surrounding the parallel conical surfaces leaving a small gap between the circular cylindrical surface and the wider edges of the conical surfaces of the foam breaker. The width of the gap depends largely upon the particular design of the foam breaker as well as the composition of the foam. The precise determination of the desired gap between the circular cylindrical surface and the edges of the conical surfaces is within the skill of the centrifuge designer.

Yet another variation of the apparatus embodiment of this invention provides for a funnel-type surface connected to the circular cylindrical surface constituting the solid/liquid centrifuge. This funnel-type unit is attached with its wider rim to the lower edge of the circular cylindrical surface. First conduit means are connected to an area near its center whereas the second conduit means are connected to the funnel near its upper edge. Preferably the second conduit means are arranged for a tangential withdrawal of solid enriched fluid spinning down in said circular cylindrical centrifuge.

Further details of the preferred apparatus in accordance with this invention will become apparent from the following description of the drawing.

FIG. 1 schematically and partly in cross section shows a fermentation apparatus 1. This fermentation apparatus 1 comprises a vessel 2 containing a similar fermentation or reaction zone 3 therein. The vessel 2 may be of any suitable structure including turbine type, stirred tank type and draft tube type fermenters. The latter type fermenter has mounted therein a draft tube 5 having an upper and a lower end 6 and 7 respectively.

A feed supply unit 9 is operatively connected with the vessel 2 for injection of feedstock via line 10. Feedstock can be introduced via pump 11 from supply vessel 12.

Oxygen containing gas such as air can be injected into the fermentation vessel 2 via line 13 which ends within the turbine 14. This turbine 14 can be put into rapid rotation by means of motor drive 15. The rapidly spinning turbine 14 brings the oxygen in finely divided form in contact with the fluid nutrient introduced via line 10 thus generating a three phase mixture within the space 3 comprising nutrient liquid, solid microorganism and oxygen containing gas. This three phase mixture from the lower portion to the upper portion of the ring space is formed between the vessel 2 and the draft tube 5. Near the upper end of the draft tube 5 the three phase mixture separates into a foam rising above the upper end of the draft tube 6 and a fluid stream essentially depleted of gas bubbles which circulates down through the draft tube 5 from its end 6 towards its end 7. The foam rises up further and into contact with the foam breaker 20.

The foam braker 20 comprises a plurality of conical surfaces 21. These conical surfaces 21 are parallel to each other leaving a space between them. These spaces 22 are in fluid communication with the interior of a hollow pipe 23 to which the conical units 21 are attached. The hollow pipe 23 and the conical surfaces 21 can be put into rapid rotation by means of a motor drive unit 24.

During the operation the foam rises from the lower portion of the vessel to in the annular space between the vessel tube and the draft tube 5 from the lower portion of the fermenter toward the top. The liquid is recirculated automatically at the upper end of the draft tube 5 toward the bottom thereof. Foam rises further and finally gets into contact with the foam breaker surfaces 21. The rapidly spinning surfaces 21 break the foam and allow an essentially liquid free gas stream to leave through pipe 23. The remaining fluid comprises a liquid nutrient phase and a solid organism phase. This fluid leaves the spinning foam breaker surfaces 21.

In accordance with this invention a cylindrical centrifuge 30 is arranged surrounding the foam breaker 20. This centrifuge surface 30 preferably is arranged stationary within the vessel 2 and can be attached to the vessel 2 by means of supporting rods 31. The centrifuge cylinder 30 at the lower end thereof is attached to a funnel line cone 32. At the lower end this cone is connected via a valve 33 to two conduits 34 and 35. Near the circumference of the centrifugal cylinder 30 and close to the lower end thereof another conduit 36 is provided for. This conduit 36 preferably is connected to the centrifugal unit 30, 32 in such a manner as to allow tangential or essentially circumferential injection or withdrawal of materials from the interior of the centrifugal unit.

During the operation of the foam breaker 20 in connection with a centrifuge 30 the fluid phase comprising the liquid nutrient phase and the solid organism phase leaving the conical surfaces 21 at a high speed and essentially in tangential direction is propelled into contact with the interior of the centrifugal cylindrical surface 30 surrounding the edges of the conical surfaces 21 at a small distance. The fluid particles therefore contact the interior of the cylindrical surface 30 in essentially a tangential direction. Thereby a fluid flow in circumferential direction along the cylindrical wall 30 of this two phase fluid is generated. This circumferential flow in turn creates a centrifugal separation or partial separation of the liquid phase and the solid phase. Thus, in the area close to the wall of the centrifugal surface 30 the solid organism phase will be enriched whereas the liquid nutrient phase depleted of solids will be flowing down in the essential portion of the centrifugal surface 30.

Depending upon the position of the valve 33 the nutrient liquid will leave the centrifugal unit 30, 32 via conduit 34 or 35. The nutrient liquid leaving through conduit unit 34 flows back into the draft tube 5 and is reused in the fermentation process. If desired, the nutrient fluid can also be removed from the fermenter via conduit 35. One of the advantages of the present invention resides in the fact that the liquid nutrient phase depleted of solid organisms can be left in the fermenter during the entire operation. This fluid therefore does not have to be resterilized in order to be again used in the fermentation.

A fluid or paste enriched in solid organisms is withdrawn from the centrifugal unit 30, 32 via conduit 36. This organism rich phase is then subjected to standard workup procedures such as a washing and separating in a washing centrifuge 40. The washed solid organism phase then is dried in a dryer 41 and finally withdrawn via line 42 as the product of the process. Wash fluid is introduced into the washing centrifuge 40 via line 43 and liquid containing the removed nutrient fluid is removed from the washing centrifuge 40 via line 44. This liquid can be reintroduced after a workup and sterilizing operation in unit 45 via conduit 46 into the fermentor 2.

It is to be noted that the cells or organisms are concentrated in the foam during the fermentation. Therefore, in accordance with one embodiment of this invention it is contemplated to withdraw the fluid comprising a liquid nutrient phase and a solid organism phase which has been collected from the foam breaker without any centrifugal enriching operation from the fermenter. Since in a foam filled fermenter the use of a foam separating device is required to allow the gas to be exhausted and to break the foam, a fluid with a high concentration of cells can be continually removed from the fermenter by collecting the spinoff fluid from the mechanical foam separating device. The solids are spun off from the mechanical foam breaker to a collecting device and this device passes the cells and the spent medium to a recovery system. The defoamed gas is vented continually. For this type of operation a collecting device is positioned so that the cells from the foam breaker spin down to a harvest valve trap which opens on command, for instance responsive to the weight load, thereby allowing the recovery of a cell concentrate. The circulation of the liquid through the draft tube is maintained for the growth of the culture. This embodiment as all the other embodiments of this invention allow the operation under stationary conditions, i.e. under conditions where the total withdrawal from the fermentor equals the total addition to the fermenter mass-wise.

Another embodiment of this invention is shown in FIG. 2. In this Figure, only the additional elements that are different from the embodiment shown in FIG. 1 have been characterized with reference numerals. In the apparatus shown in FIG. 2 the turbine 14 is supported on both sides by a bearing 14a and 14b. Similarly, the foam breaker 20 is supported by an upper and a lower bearing 20a and 20b respectively. This arrangement allows a more stable construction and operation.

Reasonable variations and modifications which will become apparent to those skilled in the art can be made in this invention without departing from the spirit and scope thereof.

I claim:
1. In a fermentation apparatus comprising
(a) a housing

(b) at least one feed conduit for the introduction of materials into said housing, (c) at least one product conduit for the removal of product from said housing, (d) a foam breaker in the upper portion of said housing (e) a gas outlet operatively connected to said foam breaker for allowing the removal of gas from said fermenter, the improvement comprising (f) a fluid collector operatively associated with respect to said foam breaker and at a small distance from said foam breaker, allowing the collection of at least a portion of the fluid leaving said foam breaker and (g) conduit means operatively associated with said collecting unit allowing the withdrawal of at least a portion of the fluid so collected from said housing.

2. Apparatus in accordance with claim 1 wherein said fluid collector comprises a solid/liquid centrifuge arranged within said housing and operatively connected to said foam breaker for receiving fluid from said foam breaker.

3. Apparatus in accordance with claim 2 wherein (a) said foam breaker comprises a first solid surface rotatably arranged in said upper portion of said housing, (b) drive means are operatively connected to said first solid surface for allowing the rapid rotation of said first solid surface, (c) a second centrifuge surface is arranged within said housing surrounding said first solid surface and in such a way as to be contacted essentially tangentially by fluid comprising liquid and solid materials spun off from said first solid surface.

4. An apparatus according to claim 3 comprising first conduit means operatively connected with said second centrifuge surface for receiving therefrom a first fluid stream rich in liquid phase but depleted in the heavier solid phase and second conduit means operatively connected to said second centrifuge surface for receiving a second fluid stream depleted in liquid phase but rich in the heavier solid phase.

5. Apparatus in accordance with claim 4 wherein said first solid surface comprises a plurality of axially spaced apart parallel conical surfaces connected to an axial tube, fluid connection being provided between the spaces between said conical surfaces and the interior of said axial tube, and wherein said second centrifuge surface is an essentially circular cylindrical surface coaxially surrounding said parallel conical surfaces leaving a small gap between said circular cylindrical surface and the outer edges of said conical surfaces.

6. Apparatus in accordance with claim 5 wherein said circular cylindrical surface communicates at its lower edge with a coaxial funnel having said first conduit means connected to an area near its center and wherein said second conduit means is operatively connected to either the lower portion of said circular cylindrical surface or said funnel near the upper edge thereof.

7. Apparatus in accordance with claim 2 comprising (a) an essentially cylindrical housing, (b) coaxially in the upper portion of said housing a mechanical foam breaker, (c) surrounding said mechanical foam breaker a stationary cylindrical centrifuge surface leaving a gap between the edge or edges of said foam breaker and said stationary cylindrical centrifuge surface.

8. Apparatus in accordance with claim 7 further comprising (a) a coaxially rotatably arranged gas injector permitting the injection of gas into the mass surrounding said injector while generating a radially outwardly directed movement onto the product located near the axis of the housing, said gas injector being arranged in the lower portion of said housing, (b) an open ended draft tube coaxially arranged between said foam breaker and said gas injector said draft tube being arranged and designed for guiding a fluid stream depleted of gas bubbles down from the upper portion of said housing toward said gas injector inside of said draft tube, said draft tube leaving sufficient ring space between the draft tube and the inner surface of said housing for the upward movement of a mixture of gas bubbles and fluid containing liquid nutrient phase and solid organism phase.

9. Apparatus in accordance with claim 6 wherein said first conduit means extends toward and opens into the lower section of the housing.

10. Apparatus in accordance with claim 6 wherein said first conduit means extends down into said draft tube and opens into the upper half of said draft tube.

11. Apparatus in accordance with claim 2 comprising valve means operatively connected with said first and/or second conduit means allowing the control of flow rate through said conduit means.

* * * * *